United States Patent [19]

Parenteau et al.

[11] Patent Number: 5,827,641
[45] Date of Patent: *Oct. 27, 1998

[54] IN VITRO CORNEA EQUIVALENT MODEL

[76] Inventors: Nancy L. Parenteau, 12 Bell Vista Rd., Brookline, Mass. 02146; Valerie Susan Mason, 28 Old Pickard La., Littleton, Mass. 01460; Bjorn Reino Olsen, 58 Vose Hill Rd., Milton, Mass. 02186

[*] Notice: The term of this patent shall not extend beyond the expiration date of Pat. No. 5,374,515.

[21] Appl. No.: 337,830

[22] Filed: Nov. 8, 1994

Related U.S. Application Data

[63] Continuation-in-part of Ser. No. 974,740, Nov. 13, 1992, Pat. No. 5,374,515.

[51] Int. Cl.$^6$ .............................. A01N 1/02; C12N 5/00
[52] U.S. Cl. ................ 435/1.1; 435/240.2; 435/240.23; 435/240.241; 424/93.7
[58] Field of Search ....................... 435/240.2, 1, 240.23, 435/240.241, 1.1; 424/93.7

[56] References Cited

U.S. PATENT DOCUMENTS

| | | | |
|---|---|---|---|
| 4,485,096 | 11/1984 | Bell | 514/21 |
| 4,546,500 | 10/1985 | Bell | 435/1 |
| 4,760,020 | 7/1988 | Neufeld et al. | 435/29 |
| 5,131,907 | 7/1992 | Williams et al. | 435/240.2 |
| 5,374,515 | 12/1994 | Parenteau et al. | 435/1 |

OTHER PUBLICATIONS

Xie, L., et al., *Developmental Biology* 25:20–22 (1989).
Simmons, S.J., et al., *Toxicology and Applied Pharmacology* 88:13–23 (1987).
Zieske, J.D., Bukusoglu, G., and Yankauckas, M.A., *Invest. Ophthalmol. & Vis. Sci.* 33:143–152 (1992).
Schermer, A., et al., *J. Cell Bio.* 103:49–62 (1986).
Muragaki, Y., et al., *Eur J. Biochem.* 207(3):895–902 (1992).
Insler, M.S., et al., *Curr. Eye Res.* 5(12):967–972 (1986).
Roat, M.I. and Thoft, R.A., *Int. Opthalmol. Clin.* 28(2):169–174 (1988).
Parish, W.E., *Fd. Chem. Toxic.* 23:215–227 (1985).
Gordon, V.C. and Kelly, C.P., *Cosmetics & Toiletries* 104:69–74 (1989).
Goldberg, A.M., *Fd. Chem. Toxic.* 23:205–208 (1985).
Shopsis, C., et al., *Fd. Chem Toxic.* 23:259–66 (1985).
Eliason, J.A. and Elliott, J. P., *Investigative Ophthalmol. & Visual Science* 28:1963–60 (1987).
Trinkaus–Randall, V., et al., *Investig. Ophthal. & Visual Science* 29:1800–1809 (1988).
Sundar–Raj, C.V., et al., Investigative Ophthalmol. Vis. Sci. 19:1222–30 (1980).

*Primary Examiner*—Sandra E. Saucier
*Attorney, Agent, or Firm*—Hale and Dorr

[57] ABSTRACT

This invention is directed to an organ equivalent of the cornea part of the eye made using tissue culturing systems. The method of constructing the cornea equivalent results in a structure analogous to the eye cornea in vivo. The cornea equivalent is an in vitro model of the eye, which can be used for transplantation or implantation in vivo or for screening compounds in vitro. This invention is also directed to the use of endothelial cells in other tissue and organ equivalents to promote basement membrane development. The cornea equivalent comprises an inner endothelial cell layer, a middle stromal cell and collagen mixture wherein the stromal cells are derived from fibroblast cells and an external epithelial cell layer, wherein the epithelial cells are derived from corneal epithelial cells.

36 Claims, 13 Drawing Sheets

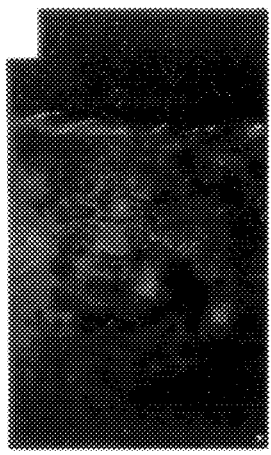   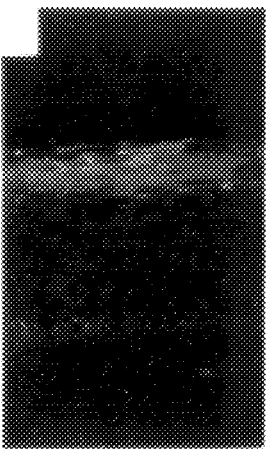
FIG.2A　　FIG.2B　　FIG.2C　　FIG.2D
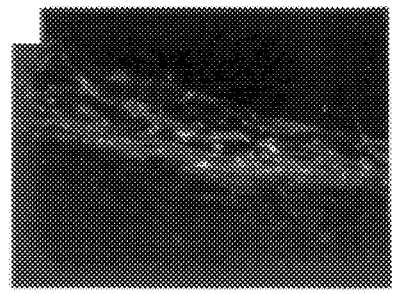 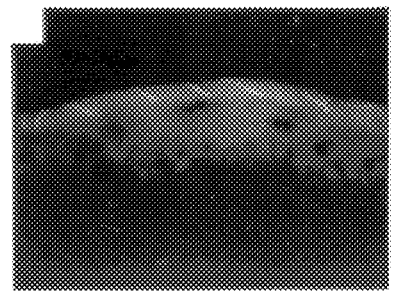 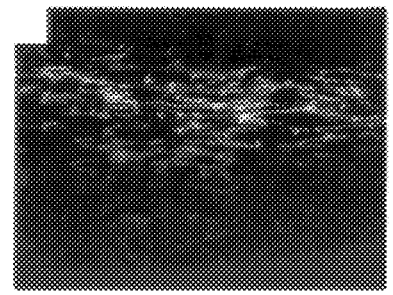
FIG.2E　　FIG.2F　　FIG.2G

IN VITRO CORNEA EQUIVALENT MODEL

CROSS REFERENCE TO RELATED APPLICATION

This application is a continuation-in-part of Pat. No. application U.S. Ser. No. 07/974,740, filed Nov. 13, 1992, now U.S. Pat. No. 5,374,515, and is incorporated herein.

FIELD OF THE INVENTION

This invention is in the field of tissue culture systems and is directed to an organ equivalent of the cornea of the eye: a cornea equivalent model. The tissue culture method of constructing the cornea equivalent model results in a construct analogous to the eye cornea in vivo. The cornea equivalent is an in vitro model of the eye, which can be used for transplantation or implantation. in vivo or for screening compounds in vitro. This invention is also directed to the use of endothelial cells in other tissue and organ equivalents to promote basement membrane development.

BACKGROUND OF THE INVENTION

Tissue culture techniques are being successfully used in developing tissue and organ equivalents. The basis for these techniques involve collagen matrix structures, which are capable of being remodeled into functional tissue and organs by employing the right combination of living cells, nutrients, and culturing conditions. Tissue equivalents have been described extensively in many patents, including U.S. Pat. Nos. 4,485,096; 4,485,097; 4,539,716; 4,546,500; 4,604, 346; and 4,837,379, all of which are incorporated herein by reference. One successful application of the tissue equivalent is the living skin equivalent, which has a morphology similar to actual human skin. The living skin equivalent is composed of two layers: the upper portion is made of differentiated and stratified human epidermal keratinocytes that cover a thicker, lower layer of human dermal fibroblasts in a collagen matrix. Bell, et al., "Recipes for Reconstituting Skin," *J. of Biochemical Engineering*, 113:113–119 (1991).

Studies have been done on culturing corneal epithelial and endothelial cells. Xie, et al., "A simplified technique for the short-term tissue culture of rabbit corneal cells," *In Vitro Cellular & Developmental Biology*, 25:20–22 (1989) and Simmons, et al., "Corneal Epithelial Wound Closure in Tissue Culture: An in vitro Model of Ocular Irritancy," *Toxicology and Applied Pharmacology*, 88:13–23 (1987). Developing an in vitro organ equivalent of the cornea of the eye is of particular interest for use in in vitro toxicity assays to serve as accurate and inexpensive non-animal predictive models of in vivo ocular and dermal irritation potential for many types of products and raw materials.

SUMMARY OF THE INVENTION

This invention is directed to an organ equivalent of the cornea of the eye. Constructing the cornea equivalent according to this invention involves the generation by tissue culture of the three distinct cell layers in the cornea: the external layer, a stratified squamous epithelium; the middle layer, collagen fibers; and the inner layer, a simple squamous epithelium, also called the corneal endothelium. The method of constructing the cornea equivalent results in a structure analogous to the eye cornea in vivo.

This invention is based, in part, on the discovery that the inclusion of an endothelial layer is required, not only for corneal transparency in vivo, but also for improved morphology, expression of biochemical and physiological markers, cell spreading, epithelial attachment to the matrix, and uniformity of epithelial coverage in vitro. The endothelium promotes basement membrane development in the cornea equivalent. The results on the influence of the endothelium in achieving a higher level of epithelial differentiation in vitro was unexpected.

Based on this discovery, it was found that the use of the endothelium in other tissue and organ equivalents also promotes basement membrane development. Thus, this invention is also directed to the use of an endothelial cells in those tissue and organ equivalent constructs that use collagen or epithelial cells.

DESCRIPTION OF THE FIGURES

FIGS. 2A, 2B, 2C, 2D, 2E, 2F, and 2G are immunofluorescence photomicrographs of corneal equivalents showing the distribution of ZO1 protein in corneal equivalents with an endothelial cell layer from various species and sources. Positive MCE controls (FIG. 2F, Mag.=375X) and DVEC (FIG. 2A, Mag.=375X) showed a striking localization in the uppermost layers of epithelium. SCE2 (FIG. 2C, Mag.= 375X) and SEC 023VC (FIG. 2D,Mag.=375X) cultures also showed limited distribution, while HUVEC (FIG. 2B,Mag.= 375X), BCE (FIG. 2E,Mag.=375X) and SEC 006A (FIG. 2G,Mag.=375X) cultures showed widely distributed staining indicating lack of specialized localization of the ZO1 protein.

FIG. 3A is a transmission electron micrograph showing formation of basal lamina in a tri-layered construct made using transformed mouse corneal endothelial cells (MCE). After seven days at the moist interface, basal lamina was observed at the stromal-epithelial junction with numerous hemidesmosomes (asterisk), anchoring filaments (small arrowheads), a well-defined lamina densa (large arrowheads) and anchoring fibrils (small arrow). Bar=0.2 µm.

FIG. 3B is a transmission electron micrograph showing formation of basal lamina in a tri-layered construct made using non-transformed sheep corneal endothelial cells (SCE2). After 7 days at the moist interface, a basal lamina was observed at the stromal-epithelial junction with hemidesmosomes (asterisk), anchoring filaments (small arrowheads) and a lamina densa (large arrowheads). Bar=0.2 µm.

FIG. 3C is a transmission electron micrograph showing spotty (patchy) basal lamina in a tri-layered construct made using non-transformed sheep arterial endothelial cells (SEC 006A). After 7 days at the moist interface, a basal lamina consisting of hemidesmosomes (asterisk) and lamina densa (arrowhead) was observed at the stromal-epithelial junction. Bar=0.2 µm.

FIG. 9A is a transmission electron micrograph showing vermiform ridges on the epithelial surface of the submerged culture at 13 days (equivalent to 6 days post moist air-lift). The apical cells layer expresses vermiform ridges along the anterior surface (arrowheads). Bar=0.5 μm.

FIG. 9B is a transmission electron micrograph showing formation of basal lamina in tri-layered constructs in a submerged state at 13 days. A basal lamina was observed at the stromal-epithelial junction with numerous hemidesmosomes (asterisk), anchoring filaments (small arrowheads), a well-defined lamina densa (large arrowheads) and anchoring fibrils (arrow). Bar=0.1 μm.

FIG. 10A is a transmission electron micrograph showing the presence of a basal lamina at the stromal epithelial junction with hemidesmosomes (asterisk) and a lamina densa (large arrowhead) of a skin equivalent construct with an endothelial layer at 7 days post air-lift. Bar=0.1 μm.

FIG. 10B is a transmission electron micrograph showing rudimentary basal lamina structures (asterisk) localized to invaginations at the stromal epithelial junction of a skin equivalent construct at 14 days post air-lift without an endothelial layer. Bar=0.1 μm.

FIG. 12A is a diagram of the eye cut in a meridional plane that passes through the equator of the eye horizontally, dividing the eye into an upper and a lower half. FIG. 12B is a section through the human cornea, showing the five layers. (Diagrams from *Functional Histology*, Borysenko et al., Little Brown, publishers, pages 216–217, 1979).

DETAILED DESCRIPTION OF THE INVENTION

Figure 12A:
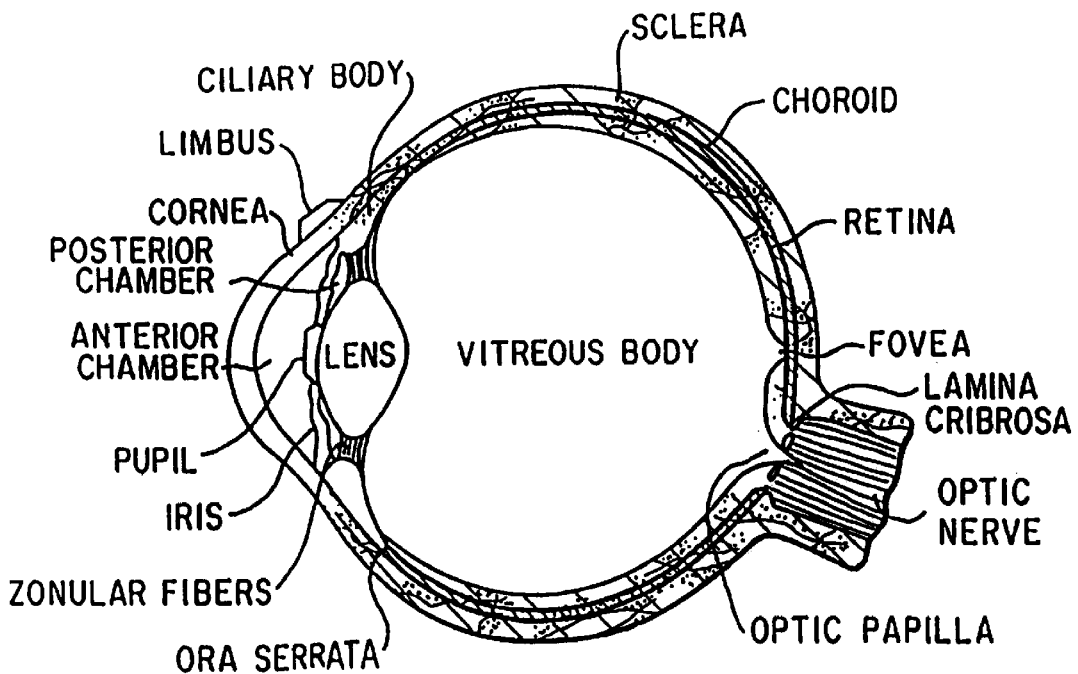
FIGS. 12A and 12B show a diagram of human eye.

The outermost layer of the eye is the fibrous tunic, composed of dense avascular connective tissue. The fibrous tunic has two different regions: the sclera and the cornea. The sclera, the "white" of the eye, forms the posterior portion of the fibrous tunic. The anterior sixth of the fibrous tunic is modified to form the transparent cornea. (FIG. 12A.) The cornea is a multilayered tissue consisting of an external epithelial layer, an underlying basement membrane, a collagenous extracellular matrix (termed the stroma), a second basement membrane (termed Descemet's membrane), and an inner single-cell-layered endothelium. Cornea epithelium is five to seven cell layers, with a single layer of columnar basal cells, two to three cell layers of wing cells, and two to three cell layers of flattened supeficial cells. At the boundary of the cornea is a transition zone (the limbus), which is the interface between the corneal and conjunctival epithelium.

Figure 12B:
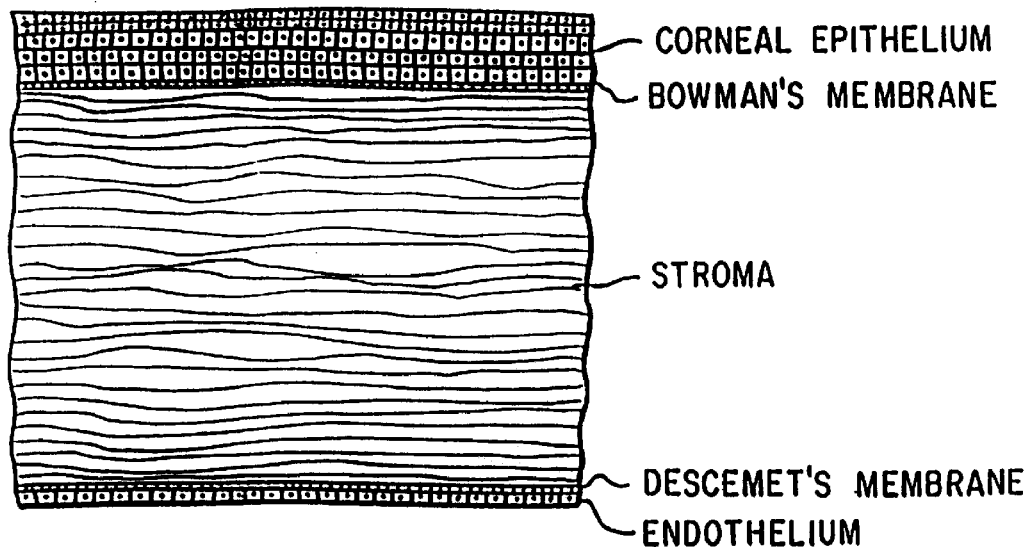

The external stratified squamous epithelium, merges with the ocular conjunctiva at the sclera-cornea junction. A simple squamous epithelium, also called the corneal endothelium, lines the inner face of the cornea. The middle layer of the cornea is clear, the result of the regular arrangement of its collagen fibers. (FIG. 12B.)

Basement membranes are specialized extracellular matrices which function to support cells, and appear to be involved in molecular sieving as well as regulation of cell attachment, growth, and differentiation. These functions involve the binding of cells to the basement membrane through a group of binding proteins that include the integrin family. However, the mechanisms involved in the assembly of a basement membrane are not known. It has been found that the basement membrane assembly regulates the differentiation of epithelium and basement membrane formation in the in vitro tissue and organ equivalents. It has also been found that the culture environment influences corneal epithelial growth and differentiation.

1. Construction of an In Vitro Cornea Model.

Constructing the cornea equivalent according to this invention involves the tissue culturing and generation of the three distinct cell layers in the cornea: the external layer, a stratified squamous epithelium; the middle layer, collagen fibers; and the inner layer, the corneal endothelium. The method of constructing the cornea equivalent results in a structure analogous to the eye cornea in vivo.

Figure 11A:
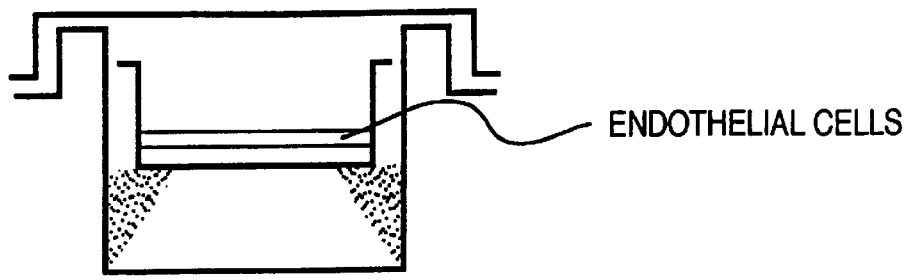
FIGS. 11A–11D show a diagrammatic representation of tissue culture model.
Figure 11B:
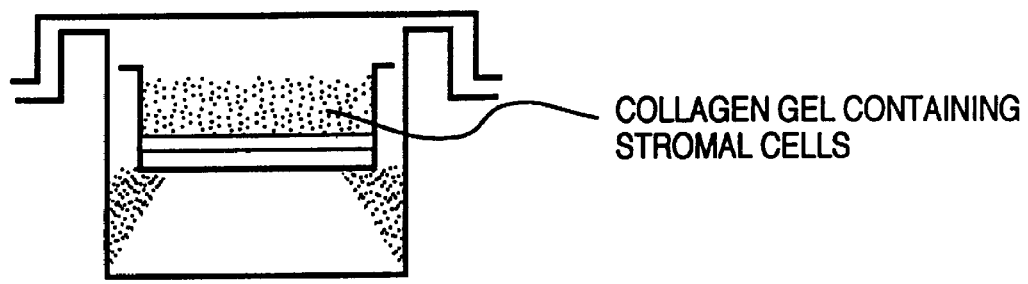
Figure 11C:
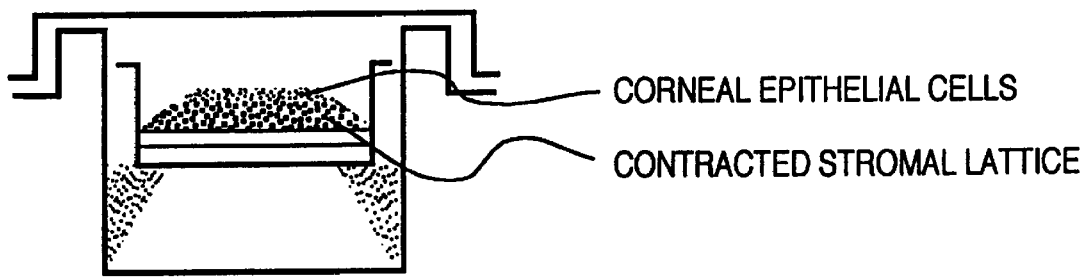
Figure 11D:
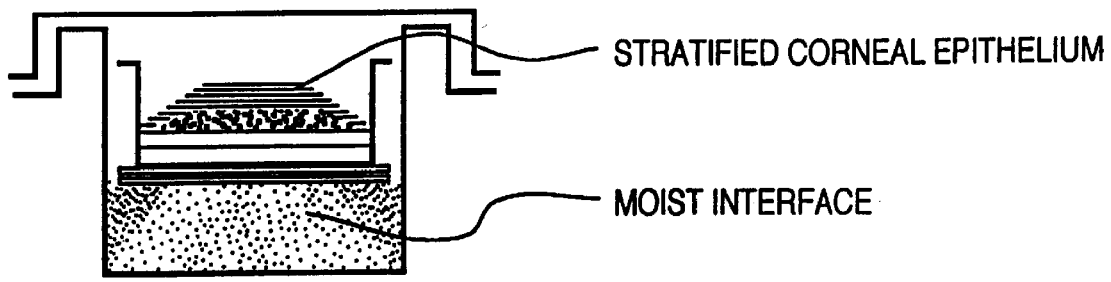

The following description of the preferred embodiment of the cornea equivalent is meant to be illustrative and not limiting. Modifications can be made to the cells and to the culturing parameters and still be within the scope of the invention. For ease of description, reference is made to FIGS. 11A to 11D, with shows a tissue culture model. In FIG. 11A, endothelial cells are seeded into a culture insert and grown to confluence. In FIG. 11B, a collagen layer containing stromal fibroblasts is cast atop the confluent endothelial cell layer and allowed to contract submerged in medium. In FIG. 11C, a suspension of corneal epithelial cells is seeded onto the central area of the contracted lattice and grown submerged until epithelial coverage of the central raised area is nearly complete. In FIG. 11D, the culture is placed at a moist air-liquid interface.

In the first step of constructing the in vitro cornea model, the endothelial cells are seeded onto membranes of a cell culture insert. These endothelial cells will form the inner layer, or basal layer, of the corneal equivalent.

The walls of the cell culture insert may consist of polystyrene, polycarbonate, resin, polypropylene (or other biocompatible plastic) with a porous membrane base of polycarbonate or other culture compatible porous membrane such as membranes made of collagen, cellulose, glass fiber or nylon attached to the bottom on which cells can be cultured. The porosity of the membrane can vary from 0.2 $\mu$m to 10 $\mu$m, with 3 $\mu$m being preferable. The insert is either suspended or supported in the culture dish to allow culture medium to access the underside of the culture. An acellular collagen layer is cast onto the cell culture membrane and allowed to gel at room temperature. The amount of acellular layer cast will depend upon the cell culture membrane used, but will typically be from 1 mL to about 5 mL.

In the preferred method, a K-RESIN® culture insert with a 3 $\mu$m porous polycarbonate membrane base approximately 2 cm$^2$ in area is used. A 1 mL acellular layer is cast onto the polycarbonate membrane and allowed to gel. The acellular collagen layer comprises 686 $\mu$g acid extracted bovine tendon collagen in 0.05% acetic acid, 8.1% 10×Minimal Essential Eagle Medium, 4 mM 1-glutamine, 50 $\mu$g/ml gentamicin, 1.8 mg/mL sodium bicarbonate and 10% Dulbecco's modified Eagle's medium (DMEM) containing 10% newborn calf serum (NBCS). Once this has gelled, 3×10$^4$ endothelial cells (6.7×10$^3$/cm$^2$) are seeded onto the gel. The endothelial layer is then submerged in DMEM containing 10% NBCS, 4 mM 1-glutamine, and 50 $\mu$g/ml gentamicin for four days at 37° C., 10% CO$_2$. Alternatively, the acellular collagen layer may be omitted and the endothelial cells seeded directly onto the porous membrane. The use of an acellular layer is preferable when using transformed endothelial cells to inhibit overgrowth of the non-contact-inhibited cells on the underside of the membrane. Alternatively, the acellular layer may be made of Type IV collagen, laminin or a hydrogel.

The endothelial cells used to form the endothelial layer can be derived from a variety of sources. Non-transformed corneal endothelial cells derived from sheep, rabbit, and cow have been used. Mouse corneal endothelial cells were transformed with large T antigen of SV40. (Muragaki, Y., Shiota, C., Inoue, M., Ooshima, A., Olsen, B.R., and Ninomiya, Y., "Alpha-1-VIII collagen gene transcripts encode a short-chain collagen polypeptide and are expressed by various epithelial endothelial and mesenchymal cells in newborn mouse tissues," *Eur. J. Biochem.* 207(3):895–902 (1992).) The preferred cell types are the transformed mouse corneal endothelial cell line, or normal corneal endothelial cells derived from sheep or rabbit. Most preferable are normal rabbit corneal endothelial cells. The normal rabbit endothelial cells are derived from enzymatically dissociated corneal endothelium or from explants of cornea and are serially cultivated in MSBM medium Johnson, W.E., Meunier, S.F., Roy, C.J. and Parenteau, N.L., "Serial Cultivation of Normal Human Keratinocytes: A Defined System Studying the Regulation of Growth and Differentiation," *In Vitro Cell. Dev. Biol.* 28A:429–435 (1992)) modified by the addition of 50 $\mu$g/mL heparin and 0.4 $\mu$g/mL heparin binding growth factor-1 (MSBME). Transformed endothelial cells are cultivated in DMEM-10%NBCS.

Endothelial cells from a noncorneal origin may also be used in this invention. The noncorneal origin endothelial cells that have also been used in this invention include ovine and canine vascular and human umbilical vein endothelial cells. The endothelial cells may be transformed with a recombinant retrovirus containing the large T antigen of SV40 (Muragaki, et al., 1992, supra). Transformed cells continue to grow in the corneal equivalent and form mounds on top of the acellular layer due to their lack of contact inhibition. Non-transformed cells will form a monolayer underlying the stromal cell-collagen layer. Alternatively, normal endothelial cells may be transfected as above, but with the addition of a recombinant construct that expresses a heat sensitive gene. These transformed cells will grow in continuous culture under reduced temperature. After establishment of a confluent endothelial cell layer, the temperature can be raised to deactivate the transforming gene, allowing the cells to resume their normal regulation and exhibit contact inhibition, to form an endothelial cell monolayer similar to the non-transformed cells. Most peptides are heat sensitive (with the exception of heat shock proteins) so that there is a wide choice of peptides that can be deactivated by raising culturing temperature. Transformation in this way also facilitates the use of hard to obtain and cultivate cell types such as human corneal endothelial cells.

In the second step, collagen is mixed with keratocytes (stromal fibroblast cells) to achieve cell-collagen mixture. The cell-collagen mixture contains approximately 100 stromal fibroblast cells per $\mu$g acid extracted bovine tendon collagen. The fibroblasts contract the gel to form a raised area (mesa) of approximately 2.5 cm$^2$. The stromal cell-collagen mixture comprises the middle layer of the cornea equivalent.

The types of collagen that can be used are acid extracted bovine tendon collagen, enzyme extracted bovine tendon collagen, or rat tail collagen. Alternatively, the collagen may also consist of a mixture of Types I and III collagen as commonly extracted from dermis or a mixture of Types I, V and VI as extracted from corneal stroma. Preferably, purified acid-extracted Type I collagen extracted from bovine tendon is used for the initial gel. In the organotypic construct, the stromal fibroblasts will synthesize additional collagen types such as V and VI as well as additional Type I collagen as they modify the collagen matrix during cultivation.

The epithelial cells will contribute Type IV and VII collagen at the epithelial-stromal junction and the endothelial cells will contribute Type XII collagen and other components of Descemet's membrane at the endothelial-stromal junction. (Muragaki et al., 1992, supra.)

Any mammalian stromal fibroblast may be used in this cell layer. Any connective tissue fibroblast such as those derived from sclera, dermis, tendon, or fascia may be used. When corneal cells are used, fibroblasts derived from rabbit or human corneal stroma are preferable. The cells are enzymatically dissociated from normal corneal stroma, cultured in DMEM-10% NBCS and serially passaged. The cells incorporated into the construct are preferably used at passage four.

Once the endothelial cell culture is ready, to prepare for the second layer of cells, the cell-collagen mixture, the medium is removed from the cell culture inserts containing the confluent endothelial layer (typically 1.7–2.5×10 5cells/insert). The cell-collagen mixture is transferred and contacted with the surface of the endothelial cell layer. The cell-collagen mixture contains the same proportions of materials as the acellular layer with the addition of $5 \times 10^4$ stromal fibroblasts/mL cast mixture. Three mL of this mixture is pipetted into each cell culture insert and allowed to gel. The construct is then submerged in DMEM-10% NBCS and allowed to contract at 37° C., 10% $CO_2$ for seven days.

These two layers, which will eventually comprise the endothelial layer and the collagen layer of the cornea model, are cultured under conditions, known to those of skill in the art, to form a condensed collagen lattice, preferably by submerging in Dulbecco's-10% NBCS at 37° C., 10% $CO_2$ for seven days, to form a central raised area or a "mesa," resulting from the contraction of the collagen by the stromal fibroblasts. Normal rabbit stromal fibroblasts are cultured for seven days, but culture times may be shorter or longer (normally 2–10 days) depending on the species, cell type and number used. DMEM 10% NBCS is the preferred culture medium but any medium which normally supports the growth of fibroblasts may be used.

In the third step, once the condensed collagen lattice is formed, corneal epithelial cells are plated onto the raised area of the collagen to form the apical, or external, layer of the cornea equivalent. The corneal epithelial cells can be derived from a variety of mammalian sources. The preferred epithelial cell is a rabbit or human corneal epithelial cell (corneal keratinocyte) but any mammalian corneal epithelial cell may be used. Other epithelial cells or keratinocytes such as those derived from the sclera (outer white opaque portion) of the eye or epidermis may be substituted, but corneal epithelial cells are preferable.

The medium is removed from the culture insert (containing the contracted stromal matrix and endothelial layer) and its surround. Normal rabbit corneal epithelial cells, passage 4, are trypsinized and seeded on top of the membrane at a density of $7.2 \times 10^4$–$1.4 \times 10^5$ cells/cm$^2$. The constructs are then incubated without media for four hours at 37° C., 10% $CO_2$ to allow the epithelial cells to attach. After the incubation the constructs are submerged in Corneal Maintenance Medium (CMM) (Johnson et al., 1992, supra.)

The epithelial cells are cultured until the mesa is covered with the epithelial cells. Completeness of epithelial coverage can be ascertained by a variety of methods, for illustration by staining the culture with a solution of Nile Blue sulfate (1:10,000 in phosphate buffered saline).

Once the mesa is covered, after approximately seven days, the constructs are aseptically transferred to new culturing trays with sufficient cornea maintenance medium (CMM) to achieve a fluid level just to the surface of the construct to maintain a moist interface without submersion of the epithelial layer. The constructs are incubated at 37° C., 10% $CO_2$, and greater than 60% humidity, with the CMM, making media changes, as necessary, typically, three times per week.

As used herein, the term "moist interface" is intended to mean a culture environment which is regulated so that the surface of the construct is moist, with high humidity, but not dry or submerged. The exact level of moisture and humidity in the culture environment is not critical, but it should be sufficiently moist and humid to avoid the formation of cornified cells. A moist interface can be characterized as trying to duplicate similar moisture levels of the human eye.

Immunocytochemical comparison of incubation of the construct at (1) a true air interface (dry) versus (2) incubation submerged versus (3) incubation at a moist (but not submerged) interface showed that environment was independent for yielding an epithelium which approached normal cornea. Incubation at a dry interface, however, caused the corneal epithelium to undergo abnormal squamous (skin-line) differentiation.

There are several alternatives to achieve a moist interface of the epithelial layer and the media. An alternative method of achieving a moist interface at the epithelial layer utilizes a lipid/mucin mixture to simulate tear film. The specialized tear film may be formulated using a physiologic buffered salt solution containing protein-lipid surfactants or lipids and/or mucin, glycoasaminoglycans, hyaluronic add or other moisture holding substance. The film droplet is placed on top of the mesa to maintain a moist barrier between the epithelium and the atmosphere. The film is typically replaced when the media is changed. Alternatively, one or more of the components of the tear film can be added directly to the medium and allowed to wick over the surface of the construct during culturing to form the moist surface interface.

Alternatively, maintenance of a moist interface may also be aided by the use of an artificial layer which can draw and hold moisture over the surface of the culture. This can be achieved by the application of a thin layer made of agarose, hydrogel, or alginate.

In another alternative, a moist interface can be achieved using a dialysis membrane or polymer, such as contact lens material, cut slightly larger than the mesa, may be used to draw and hold fluid and prevent moisture loss.

2. Use of the Endothelium in Other Organ Equivalents.

The inclusion of an endothelial layer promotes improved morphology, expression of biochemical and physiological markers, cell spreading, epithelial attachment to the matrix, and uniformity of epithelial coverage in vitro. The results on the influence of the endothelium in achieving a higher level of epithelial differentiation in vitro and promoting basement membrane formation was applied in other tissue equivalent in vitro culturing methods.

Examples of tissue equivalents that can be modified according to this invention include, U.S. Ser. No. 08/193,809, incorporated herein by reference, and specifically dermal and skin equivalents. In general, to make a skin equivalent, passaged dermal fibroblasts are mixed with type I collagen to form a cellular collagen lattice inside a culture insert. This lattice then served as a substrate for epidermal keratinocytes. The keratinocytes grow to confluence and stratify while the culture remains submerged in culture medium for the first 4 days. The skin equivalent is then cultured at the air-liquid interface to allow differentiation of the epidermis to proceed.

In preparing tissue or organ equivalents using collagen according to this invention, a first layer of endothelial cells can be cultured, as described above in section one, prior to casting collagen onto the endothelial layer. In a preferred embodiment, the endothelial cell layer is used to modify in vitro skin equivalent models, such as those described in U.S. Pat. No. 4,485,096, incorporated herein by reference, to promote epithelial differentiation and basement membrane formation.

3. Uses For The Cornea Equivalent Model.

The Draize eye irritation test has served as the standard for evaluating a product's ocular irritation potential for the past forty-five years. (Draize, J.H., Woodard, G., Calvery, H.O., "Methods for the study of irritation and toxicity of substances applied topically to the skin and mucous membranes," *J. Pharmacel. Exp. Ther.* 82:377–390 (1944).)

A variety of test models and protocols have been proposed as in vitro screens for assessing ocular irritation. (Booman, K.A., De Prospo, J., Demetrulias, J., Driedger, A., Griffith, J.F., Grochoski, G., Kong, B., McKormick ,W.C., North-Root, H., Rosen, M.G., Sedlak, R.I., "In vitro methods for estimating eye irritancy of cleaning products, Phase I: Preliminary assessment," *J. Toxicel.Cut & Ocular Toxicol.* 7:173–185 (1988).) Cell cultures used in conjunction with quantifiable, objective endpoints for assessing cytotoxicity have shown good correlation to in vivo data sets. (Bruner, L.H, Kain, D.J., Roberts, D.A., Parker, R.D., "Evaluation of seven in vitro alternatives for ocular safety testing," *Fund. Appl. Toxicol.* 17:136–149 (1991).) However, cells in monolayer culture have inherent limitations as model systems for predicting irritation in complex organs such as the eye. Typically, cells in monolayer culture are susceptible to irritants at concentrations far below those required to induce irritation in vivo. Test samples must first be solubilized in cell culture medium prior to being introduced to the culture system. This can lead to secondary toxicities due to effects on osmolarity, pH or medium components. Furthermore, artifacts arising from diluting the test sample can mask toxicity and lead to underestimating a sample's irritancy potential. The level of epidermal differentiation obtained in monolayer culture only poorly mimics the extent of differentiation observed in vivo. The protective barrier function of corneal epithelium, including cytoskeletal keratin networks, desmosomes and tight junctions, known to play an important role in protecting ocular tissue from chemical insult are not present. (Holly, F.J., "Physical chemistry of the normal and disordered tear film," *Trans. Opthalmol. Soc. U.K.* 104:374–380 (1985).) The organotypic model proposed here, overcomes some of the inherent limitations of monolayer culture by providing a model system which more closely simulates the target organ of interest. In addition, the physical configuration of this test cornea allows the topical application of test samples in vehicles (e.g., petrolatum and mineral oil) which approximate the mode of exposure in vivo.

Investigators have used both animal models and cultured cells in an effort to approximate the human condition. There is, however, a wide gap in direct applicability. Animals may be too different in their physiological response to injury and analysis using traditional cell culture may be too simplified for direct correlation to likely in vivo human responses. While these methods are necessary and useful, the use of human organotypic constructs helps eliminate the discrepancy between human and animal response, and bridges the gap between cultured cells and the complex organism. Cell-cell interactions and the response to injury or pharmacologic agents may be readily examined in a controlled, organotypic environment.

The organotypic culture method may also be used to form graftable human tissue either as an adjunct to conventional transplantation or as a substitute. The use of cultured corneal endothelial cells has already been shown to be beneficial as a replacement for the often damaged or inadequate endothelium of graft material. (Insler, M.S., Lopez, J.G., "Transplantation of cultured human neonatal corneal endothelium," *Curr. Eye Res.* 5(12):967–72 (1986).) The use of cultured corneal epithelium has also shown some benefit in promoting wound closure. (Roat, M.I., Thoft, R.A., "Ocular surface epithelial transplantation," *Int. Opthalmol. Clin.* 28(2):169–174 (1988).) The organotypic corneal construct comprising an endothelium, stroma and epithelium could be used for ocular wound closure and full-thickness repair of the cornea. Although not transparent in vitro, it is expected that the endothelial cells provided by the construct will regulate fluid transport to the corneal stroma and further stimulate the stromal fibroblasts to continue to organize the matrix and produce the appropriate collagens and glycosaminoglycans necessary for corneal clarity. The in vitro corneal equivalent may be constructed with more or less extracellular matrix or stroma to facilitate remodeling. Wound closure would be maintained by the presence of the well-adhered corneal epithelium, thereby limiting hyperproliferation and scarring of the stromal matrix.

The invention is illustrated further by the following examples, which are not to be taken as limiting in any way.

EXAMPLES

Example 1

Comparison of Normal Endothelial Cells of Various Origins

Purpose: This study was performed to determine if non-transformed endothelial cells from corneal and noncorneal origin can effect epithelial differentiation and basement membrane formation.

Materials and Methods: Transformed mouse corneal endothelial cells (MCE) described in U.S. Pat. No. 5/374,515 were compared to the following normal strains:

a. ovine corneal endothelial cells (SCE2),
b. ovine arterial endothelial cells (SEC 006A),
c. ovine endothelial cells (SEC 023VC),
d. canine vena caval endothelial cells (DVEC),
e. human umbilical vein endothelial cells (HUVEC) and
f. bovine corneal endothelial cells (BCE 15960).

As a negative control, constructs were prepared without endothelial cells.

The Corneal Maintenance Medium (CMM) consisted of a 3:1 mixture of calcium-free, Dulbecco's modified Eagle's Medium:Ham's F-12 with 1.1 $\mu$M hydrocortisone, 5 $\mu$g/mL insulin, 5 $\mu$g/mL transferrin, 20 pM triiodothyronine, $10^{-4}$ M ethanolamine, $10^{-4}$ M o-phosphoryl-ethanolamine, 1 mM strontium chloride, 50 $\mu$g/mL gentamicin, 4 mM l-glutamine, 90 $\mu$M adenine, $3\times10^{-6}$M selenium, 1.8 mM calcium chloride and 0.3% NBCS.

The endothelial cells were taken from frozen stocks and cultured one passage before use in the corneal constructs. Endothelial cells were seeded at $3.0\times10^4$ cells per transwell on a layer of acellular 1 mg/ml type I collagen gel and grown to confluence for 7 days while submerged. HUVEC, SEC 023VC, BCE 15960, and SEC 006A were cultured in Ham's F-12+10% NBCS, 25 $\mu$g/mL Heparin, 50 $\mu$g/mL ECGS and 50 $\mu$L/mL gentamicin. MCEC, DVEC, SCE2, and HEC were cultured in DMEM+10% NBCS and 50 $\mu$g/mL gentamicin while incubated at 37° C. in an atmosphere of 10% $CO_2$.

Rabbit corneal keratocytes at a density of $5.0 \times 10^5$ cells/mL in 3 mL of 1 mg/mL Type I collagen were laid on top of the endothelial layer. The collagen containing the cells gelled and medium (DMEM—10% NBCS and 50 μg/mL gentamicin) was added to the outside of the transwell. The constructs were incubated at 37° C. with 10% $CO_2$ for the following seven days while the collagen lattice containing the fibroblasts were contracted by the corneal fibroblasts.

The collagen lattices had contracted away from the sides of the transwell to form a mesa. The medium was removed from the well and 50 μL suspension rabbit corneal epithelial cells ($3.6 \times 10^6$ cells/mL) was seeded onto the center of the mesa, at $1.8 \times 10^5$ cells/mesa in CMM. 12 mL CMM was added back, submerging the entire construct. At seven days post-epithelialization, the rabbit corneal epithelial cells proliferated to completely cover the mesa.

Epithelial coverage was monitored by Nile Blue sulfate-staining. Staining was done by adding 8 mL 1:10,000 Nile Blue Sulfate in phosphate buffered saline (PBS) for 30 minutes. Adherence was tested by attempting to peel the stained epithelium from the collagen lattice with forceps. Resistance to peeling indicated a positive effect of the endothelial cell layer.

When epithelial coverage was complete, the constructs were transferred to a new tray containing two cotton pads and enough medium, 11 mL, (9 ml at feeds hereafter as the cotton pads together retain 2 mL) to just meet the surface of the culture and wick over the surface of the construct. Doing this step provided a moist apical surface to prevent abnormal squamous differentiation. The cultures were maintained in the incubator at 37° C. in 10% $CO_2$ and medium changes were made every 2–3 days for the remainder of the culture period.

Results:

Gross observations: Nile Blue sulfate staining showed complete, although varied coverage in all conditions. Qualitative peel testing indicated adherence in the MCE (positive control), and BCE cultures, slight adherence in the SEC 023VC and SCE2 cultures and no adherence in the HUVEC, DVEC, SEC 006A and no endothelium cultures at 7 days post-epithelialization.

Immunocytochemistry: Immunocytochemistry using indirect fluorescence was performed using anti-laminin antibody to detect deposition of basement membrane components, and anti-ZO1 antibody to detect distribution of tight junction-associated protein.

Figure 1A:
FIGS. 1A, 1B, 1C, 1D, 1E, and 1F are immunofluorescence photomicrographs of corneal equivalents showing the distribution of laminin in corneal equivalents with an endothelial cell layer from various species and sources. Corneal constructs after 7 days at the moist interface exhibit a small amount of laminin deposited in the basement membrane zone. HUVEC (FIG. C, Mag.=375X) and SEC 006A (FIG. 1E, Mag.=375X) cultures showed continuous distribution of laminin. DVEC (FIG. 1B, Mag.=375X), SCE2(FIG. 1D, Mag.=375X) and SEC023VC (FIG. 1F, Mag.=375X) showed nearly continuous distribution. BCE (FIG. 1A, Mag.=375X) showed a distribution similar to that previously obtained in moist cultures lacking an endothelial cell layer.
Figure 1B:
Figure 1C:
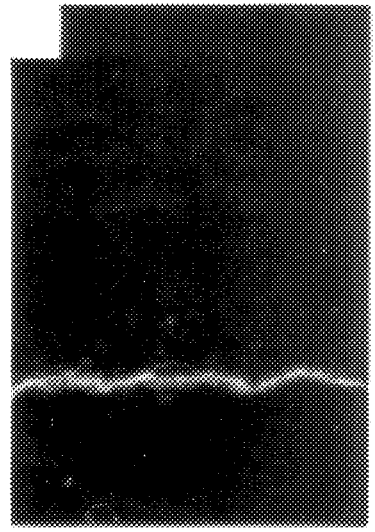
Figure 1D:
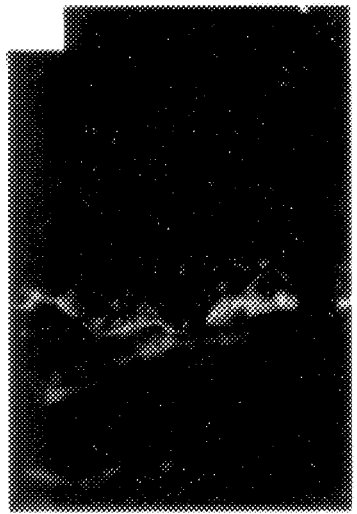
Figure 1E:
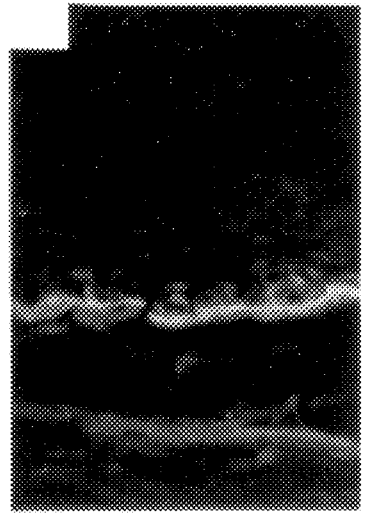
Figure 1F:
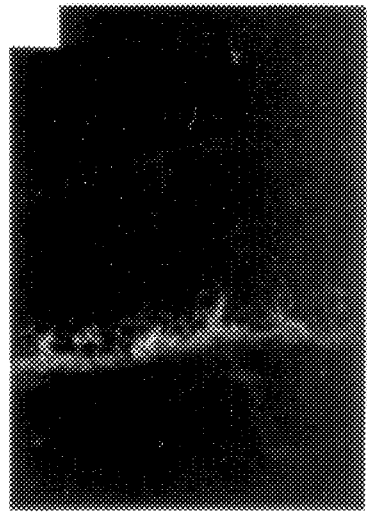

Laminin Distribution: In previous studies described in. U.S. Pat. No. 5,374,515, small amounts of laminin were localized in patches along the basement membrane zone in moist air-lift cultures lacking endothelial cells. The addition of MCE greatly enhanced laminin deposition resulting in a strongly staining, continuous distribution along the epithelial-stromal junction. HUVEC and SEC 006A cultures showed continuous distribution of laminin. DVEC, SCE2, and SEC 023VC showed nearly continuous distribution. BCE showed a distribution similar o that previously obtained in moist cultures lacking an endothelial cell layer. (See FIGS. 1A to IF).

ZO1 Distribution: ZO1 is a protein associated with tight junctions in corneal epithelium. Normal distribution should be limited to distinct areas in the upper layers of the corneal epithelium. Positive MCE controls and DVEC showed a striking localization in the uppermost layers of epithelium. SCE2 and SEC 023VC cultures also showed limited distribution, while HUVEC, BCE and SEC 006A cultures showed widely distributed staining indicating lack of specialized localization of the ZO1 protein. (See FIGS. 2A to 2G).

Figure 3A:
FIGS. 3A, 3B, and 3C are a series of transmission electron micrographs showing the effects of various strains of endothelial cells on basal lamina formation in tri-layered corneal constructs.
Figure 3B:
Figure 3C:
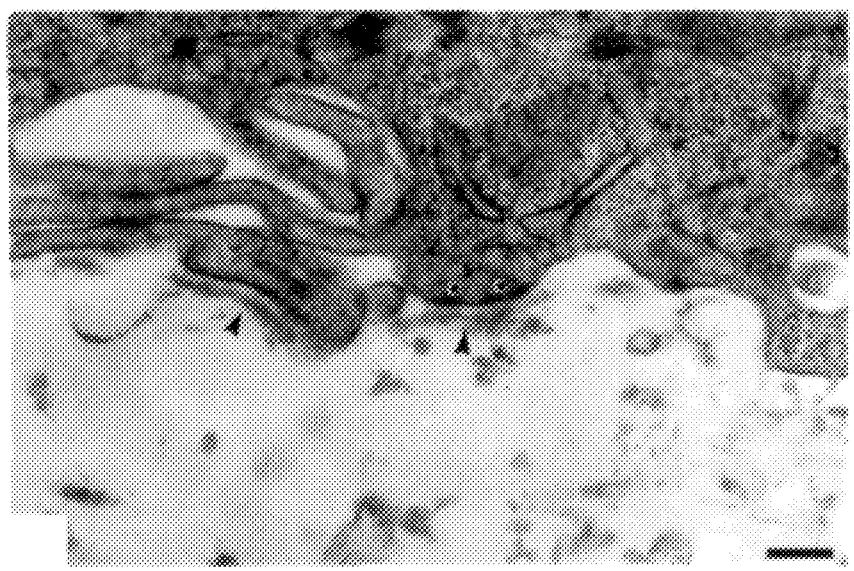

Basement Membrane Formation: The assembly of basement membrane was examined by electron microscopy. (See FIGS. 3A to 3C). MCE-containing cultures form recognizable basement membrane and well-formed hemidesmosomes. Hemidesmosomes and associated basement membrane structures were detected in SEC 006A and SCE2 containing cultures.

Conclusions: Technical difficulties associated with endothelial cell culture and survival from the various sources possibly hindered the full expression of all characteristics of a given endothelial cell strain and lead to variability in results. However, in each case, one or more of the endothelial cell strains tested mimicked characteristics achieved using the transformed MCE corneal cell line. Since there were always more MCE cells present in these cultures due to their rapid growth and lack of contact inhibition, differences are attributed to concentration effects rather than inherent inability of the various endothelial strains to produce an effect on the epithelium. Of the strains tested, SCE2 and SEC 006A cells showed the greatest ability to influence basement membrane. Epithelial differentiation appeared most affected by SCE2 and DVEC. Refinement of the culture process to suit the particular requirements for adequate growth and survival of the normal endothelial cells will lead to similar results as those obtained with the transformed mouse line in those strains showing a positive effect. The effects of endothelium on epithelial differentiation and basal lamina formation is not species specific nor limited to endothelial cells of corneal origin.

Example 2

Comparison of Moist and Submerged Cultures Containing Endotielial Cells

Purpose: This study was performed to determine if a moist interface is necessary for full expression of differentiated characteristics and formation of basal lamina.

Materials and Methods: Cultures were prepared according to the previous example using MCEC in the endothelial layer. At time of moist air-lift, a portion of the cultures were maintained submerged in culture medium. Both groups were maintained for an additional one and two weeks. Corneal constructs were examined at 14 days submerged and 7 days post moist air-lift by histology, immunocytochemistry and electron microscopy.

Figure 4A:
FIGS. 4A and 4B are immunofluorescent photomicrographs of the distribution of keratin 3 under different environmental conditions. Keratin 3 is a marker specific for corneal epithelial cells and is normally present in all suprabasal cell layers of the corneal limbus and the cells of the central cornea. (Schermer, A., Galvin, S., and Sun, T.T., "Differentiation-related expression of a major 64K corneal keratin in vivo and in culture suggests limbal location of cornea epithelial stem cells," *J.Cell. Biol.* 103:49 (1986).) The photomicrographs depict 14 day submerged (FIG. 4A, Submerged,Mag.=375X) and 7 day post moist air-lift (FIG. 4B, Moist Air-Lift, Mag.=375X) corneal constructs showing staining for keratin 3 (labeled using AE5 antibody) is strong and present in all suprabasal layers as in normal corneal limbus in vivo.
Figure 4B:
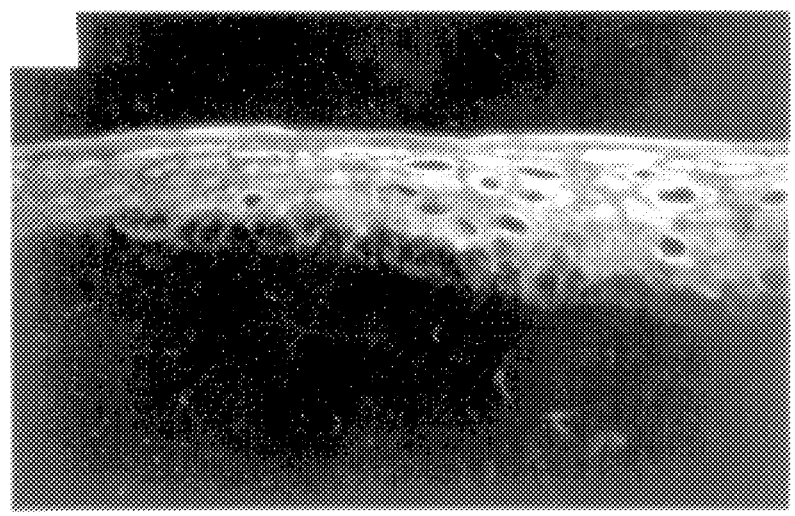
Figure 5A:
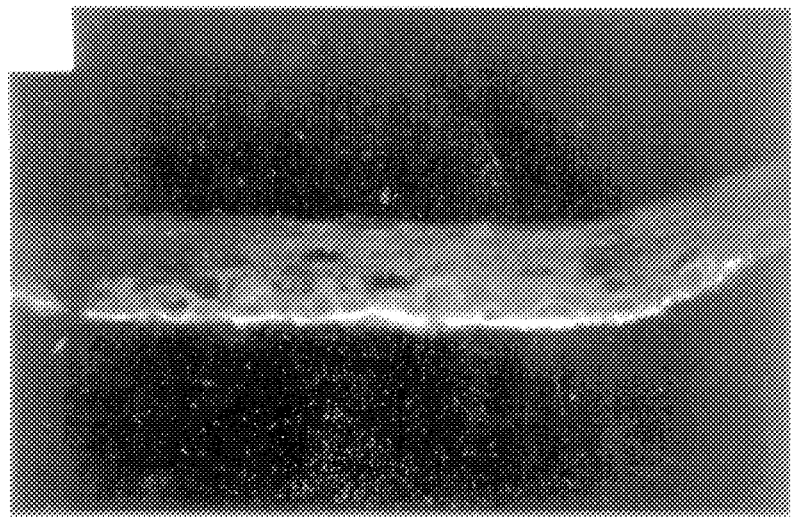
FIGS. 5A and 5B are immunofluorescent photomicrographs of the distribution of alpha$_6$-integrin under submerged or moist air-lift environmental conditions. alpha$_6$-Integrin is a marker for hemidesmosomes in corneal epithelium. The photomicrographs depict 14 day submerged (FIG. 5A, Submerged,Mag.=375X) and 7 day post moist air lift (FIG. 5B, Moist Air-Lift, Mag.=375X) corneal constructs showing alpha$_6$-integrin localization as a continuous band along the epithelial cell-matrix interface suggesting polarization of the basal epithelial cells.
Figure 5B:
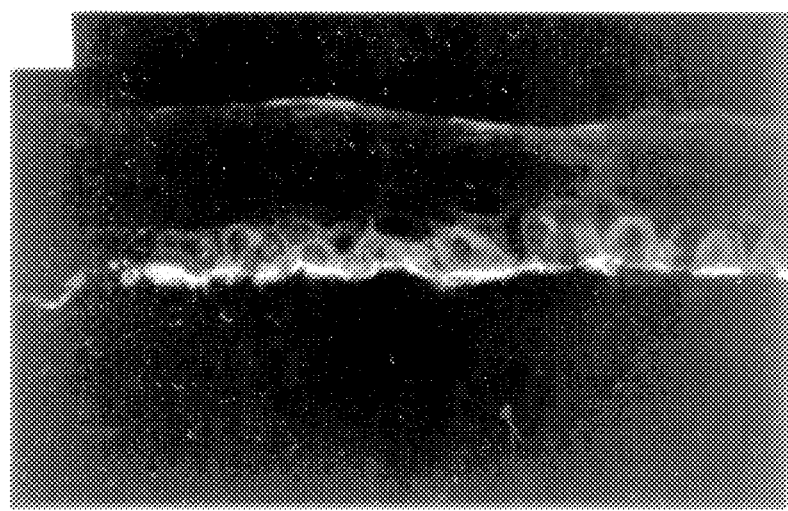
Figure 6A:
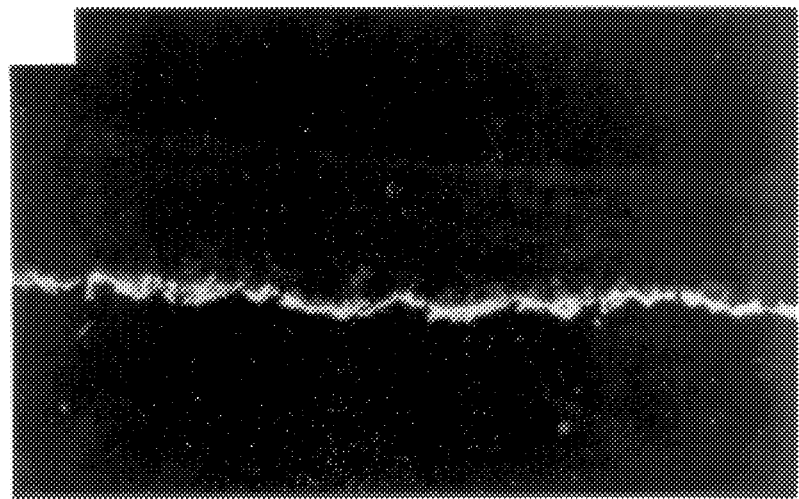
FIGS. 6A and 6B are immunofluorescence photomicrographs of corneal equivalents showing the distribution of type VII collagen in corneal equivalents in under different environmental conditions. The photomicrographs depict 14 day submerged (FIG. 6B, Submerged,Mag.=375X) and 7 day post moist air lift (FIG. 6A, Moist Air-Lift,Mag.=375X) corneal constructs showing type VII collagen in a continuous band at the stromal-epithelial junction.
Figure 6B:
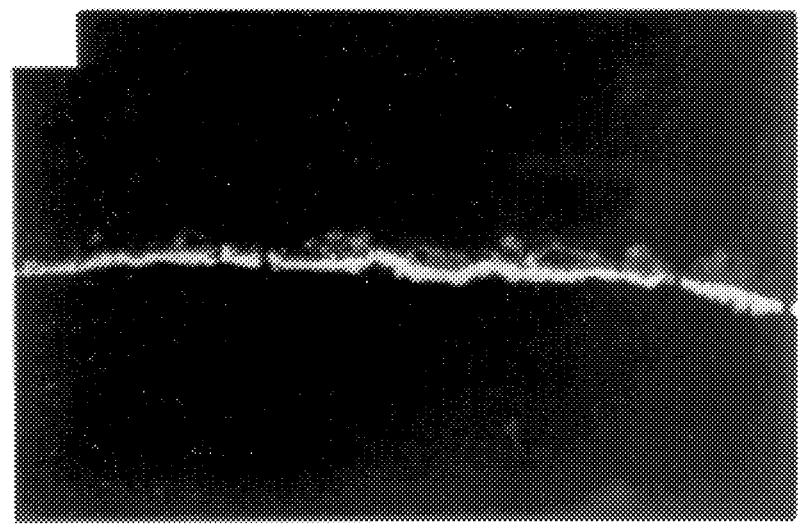
Figure 7A:
FIGS. 7A and 7B are immunofluorescence photomicrographs of corneal equivalents showing the distribution of Laminin in corneal equivalents under different environmental conditions. The photomicrographs depict 14 day submerged (FIG. 7A, Submerged,Mag.=375X) and 7 day post moist air-lift (FIG. 7B, Moist Air-Lift,Mag.=375X) corneal constructs showing exhibit a continuous band of laminin deposited at the basement membrane zone.
Figure 7B:
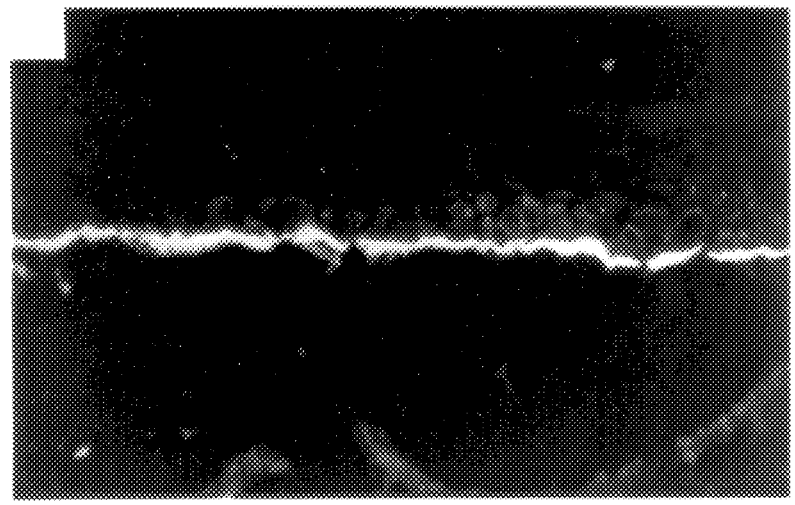
Figure 8A:
FIGS. 8A and 8B are immunofluorescent photomicrographs showing the distribution of enolase under different environmental conditions. Enolase is a marker for the proliferative cell population in corneal epithelium. It is normally present in basal cells of the limbal region. (Zieske, J.D., Bukusoglu, G., Yankauckas, M.A., "Characterization of a potential marker of corneal epithelial stem cells," *Invest. Opthalmol. Vis. Sci.* 33:143–152 (1992).) The suprabasal layers of the epithelium stain positively for enolase when the culture is 14 days submerged (FIG. 8A, Submerged,Mag.=375X) or 7 day post moist air lift (FIG. 8B, Moist Air-Lift, Mag.=375X), to more closely approximate what is observed in vivo.
Figure 8B:
Figure 9A:
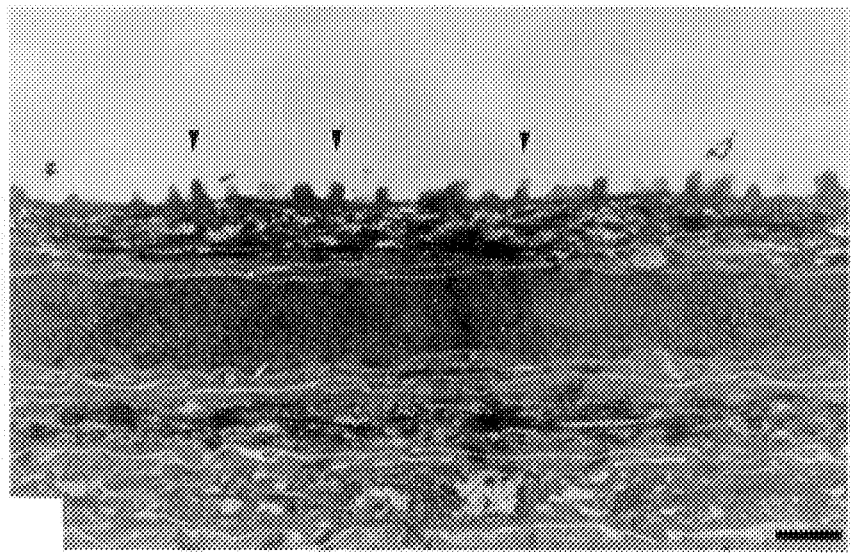
FIGS. 9A and 9B are a series of transmission electron micrographs showing ultrastructural specialization in tri-layered constructs in a submerged state.
Figure 9B:
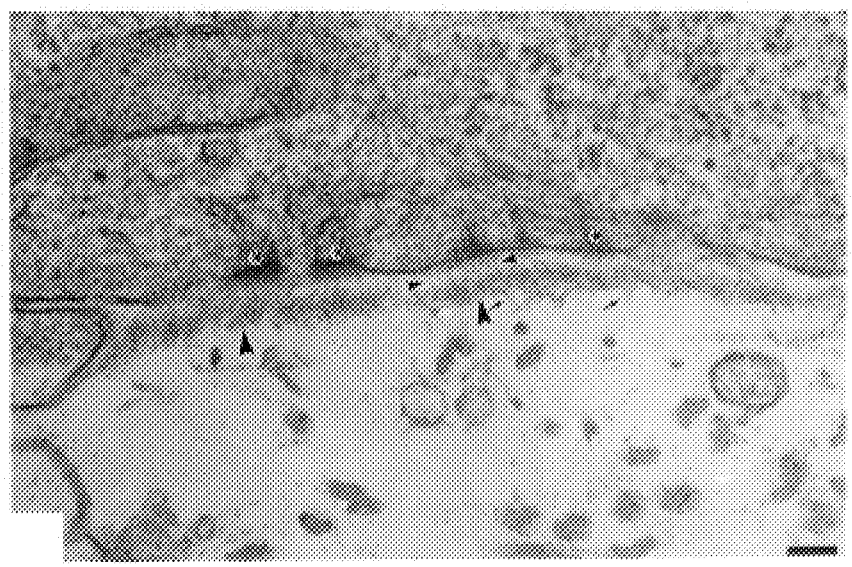

Results: Comparison of the two groups showed no differences in histology or immunocytochemical distribution of keratin 3 (FIGS. 4A and 4B), alpha-6 integrin (FIGS. 5A and 5B), Type VII collagen (FIGS. 6A and 6B), laminin (FIGS. 7A and 7B) or alpha-enolase (FIGS. 8A and 8B). Electron microscopy showed no ultrastructural differences between moist and submerged cultures: submerged cultures had vermiform ridge surface specializations (FIG. 9A) and exhibited basement membrane (FIG. 9B) identical to those seen in the standard moist cultures containing endothelium.

Conclusion: A specialized environment is not necessary to achieve full epithelial differentiation in the presence of endothelial cells.

Example 3

Examination of Endothelial Cell Effect on Skin Constructs

Purpose: This study was performed to determine if the presence of endothelial cells could basement membrane assembly in other epithelial cell types.

Materials and Methods: Human epidermal keratinocytes and dermal fibroblasts were substituted for corneal epithelial and stromal cells, respectively, in the preparation of the skin construct.

Endothelial cells were taken from frozen stocks (the transformed mouse corneal endothelial cells (MCE) from Example 1) and cultured one passage before use in the construct. Endothelial cells were seeded at $3.0 \times 10^4$ cells per transwell on a layer of acellular 1 mg/ml type I collagen gel and grown to confluence for 7 days while submerged in DMEM—10% NBCS and 50 µg/mL gentamicin while incubated at 37° C. in an atmosphere of 10% $CO_2$.

Human dermal fibroblasts (HDF), at a density of $2.5 \times 10^5$ cells/mL in 3 mL of 1 mg/mL Type I collagen, were laid on top of the endothelial layer. The collagen containing the cells gelled and medium (DMEM—10% NBCS and 50 µg/mL gentamicin) was added to the outside of the transwell. The constructs were incubated at 37° C with 10% C02 for the following seven days while the collagen lattice containing the fibroblasts were contracted by the corneal fibroblasts.

At 6 days, the collagen lattices had contracted away from the sides of the transwell to form a mesa. The media was removed from the well and a 50 µg/mL suspensions of human epidermal cells ($3.33 \times 10^6$ cells/mL) were seeded onto the center of the mesa in MSBM (3:1 Calcium-free, glucose-free DMEM:Ham's F-12 supplemented with 4 mM L-glutamine, 1.1 µM hydrocortisone, 5 µg/mL insulin, 5 µg/mL triiodothyronine, $10^{-4}$ M ethanolamine, $10^{-4}$ M, o-phosphoryl-ethanolamine, 0.18 mM adenine, $2 \times 10^{-9}$ M propesterone, $5.26 \times 10^{-8}$ M selenium, 0.3% bovine serum, 1.8 mM calcium chloride and 10 ng/mL epidermal growth factor ). MSBM medium was added back to the outside of the transwell submerging the entire construct, Constructs were returned to the incubator at 36° C./10% $CO_2$.

At four days post-epidermalization, the human epidermal cells proliferated to completely cover the mesa. Medium was removed from the inside and outside chambers. The inner chamber was removed and two cotton pads were placed in the well to raise the construct to the air-liquid interface. Medium, 11 mL cSBM with calcium (1:1 Calcium-free, glucose-free DMEM:Ham's F-12 supplemented with 4 mM L-glutamine, 1.1 µM hydrocortisone, 5 µg/mL insulin, 5 µg/mL triiodothyronine, $10^{-4}$ M ethanolamine, $10^{-4}$ M, o-phosphoryl-ethanolamine, 0.18 mM adenine, $5.26 \times 10^{-8}$ M selenium, 2.0% bovine serum, 1 ng/mL epidermal growth factor and 1.8 mM calcium chloride) was added back to the transwell containing the construct. Constructs were returned to the incubator at 35.5° C./10% $CO_2$.

Constructs were maintained in culture conditions suitable for skin equivalent culture. At four days following airlift, the medium was replaced with 9 mL maintenanceSBM with calcium (1:1 Calcium-free, glucose-free DMEM:Ham's F-12 supplemented with 4 mM L-glutamine, 1.1 µM hydrocortisone, 5 µg/mL insulin, 5 µg/mL triiodothyronine, $10^{-4}$ M ethanolamine, $10^{-4}$ M, o-phosphoryl-ethanolamine, 0.18 mM adenine, $5.26 \times 10^{-8}$ M selenium, 1.0% bovine serum, 1 ng/mL epidermal growth factor and 1.8 mM calcium chloride). Cultures were maintained at the air-liquid interface at day 4 following epidermalization. Cultures were maintained for one week at the air-liquid interface and examined for formation of basement membrane by electron microscopy at seven days post air-lift.

Figure 10A:
FIGS. 10A and 10B are a series of transmission electron micrographs showing basal lamina production in skin equivalent constructs with an endothelial layer (FIG. 10A) and without an endothelial layer (FIG. 10B).
Figure 10B:
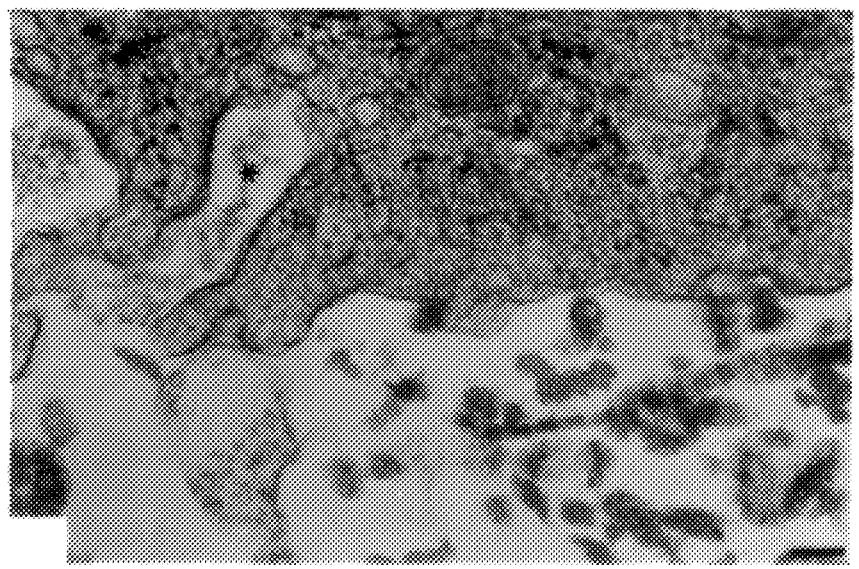

Results: Qualitative peel tests performed at the time of air-lift showed firm attachment of the epidermis to the dermal substrate. Electron microscopy of day 7 post air-lift samples with an endothelial layer (FIG. 10A) revealed basement membrane formation superior to that seen in the absence of endothelium at 14 days post airlift. Unlike corneal constructs, skin constructs cultured at an air-liquid interface without an endothelium show normal distribution of differentiation markers and continuous localization of basal lamina components but show only rudimentary basement membrane and hemidesmosome formation after weeks in culture (FIG. 10B).

These results are with an air-liquid interface. It is expected from the results of Example 2 that enhanced differentiation of submerged skin cultures would be achieved in the presence of an endothelium.

Conclusion: The presence of the endothelial cell layer enhances assembly of basement membrane by epidermal keratinocytes.

Although the foregoing invention has been described in some detail by way of illustration and example for purposes of clarity of understanding, it will be obvious to one skilled in the art that certain changes and modifications may be practiced within the scope of the appended claims.

What is claimed is:

1. A cornea equivalent comprising:
   (a) an inner endothelial cell layer,
   (b) a middle stromal cell-collagen mixture layer, wherein said stromal cells are derived from fibroblast cells, and
   (c) an external epithelial cell layer, wherein said epithelial cells are derived from corneal epithelial cells.

2. The equivalent of claim 1, wherein said endothelial cells of said inner endothelial cell layer are derived from a member selected from the group consisting of SCE2 which are ovine corneal endothelial cells, SCE 006A which are ovine arterial endothelial cells, SEC 023VC which are ovine endothelial cells, DVEC which are canine vena caval endothelial cells, HUVEC which are human umbilical vein endothelial cells and BCE 15960 which are bovine corneal endothelial cells.

3. The equivalents as in either claim 1 or claim 2, wherein said endothelial cells of said inner endothelial cell layer are transformed with the large T antigen of SV40.

4. The equivalent of claim 1, wherein said fibroblast cells of said middle stromal cell-collagen mixture layer are derived from the group comprising human dermal fibroblast cells, human corneal keratocytes, and rabbit corneal keratocytes.

5. The equivalent of claim 1, wherein said epithelial cells of said external epithelial cell layer are derived from the group comprising corneal epithelial cells and scleral epithelial cells.

6. The equivalent of claim 1, wherein said collagen in said middle stromal cell-collagen mixture layer is selected from the group consisting of acid extracted bovine tendon collagen, enzyme extracted bovine tendon collagen, rat tail collagen, Type I collagen extracted from dermis, Type III collagen extracted from dermis, Type I collagen extracted from corneal stroma, Type V extracted from corneal stroma, Type VI collagen extracted from corneal stroma, and mixtures thereof.

7. The equivalent of claim 6, wherein said collagen is a mixture of Types I and III collagen extracted from dermis.

8. The equivalents of claim 6, wherein said collagen is a mixture of Types I, V and VI collagen extracted from corneal stroma.

9. The equivalent of claim 1, wherein said middle stromal cell-collagen mixture layer is uniform in thickness.

10. The equivalent of claim 1, wherein said external epithelial cell layer is uniform in thickness.

11. The equivalent of claim 1, wherein the suprabasal cells of said external epithelial cell layer express enolase.

12. The equivalent of claim 1, wherein the suprabasal cells of said external epithelial cell layer express keratin 3.

13. The equivalent of claim 1, wherein the junction between said middle stromal cell-collagen mixture layer and said external epithelial cell layer expresses laminin and type VII collagen.

14. The equivalent of claim 1, wherein the junction between said middle stromal cell-collagen mixture layer and said external epithelial cell layer demonstrates a basement membrane.

15. The equivalent claim 1, wherein said external epithelial cell layer exhibits vermiform ridges on the epithelial surface.

16. The equivalent of claim 1, wherein the suprabasal cells of said external epithelial cell layer exhibit tight junctions between cells.

17. A method for transplanting the cornea equivalent of claim 1 into a recipient, comprising grafting said equivalent into said recipient.

18. The method of producing a cornea equivalent comprising:
   (a) culturing endothelial cells to form an inner endothelial cell layer;
   (b) mixing stromal cells with collagen to achieve a stromal cell-collagen mixture, wherein said stromal cells are derived from fibroblast cells;
   (c) contacting said inner endothelial cell layer of step (a) with said stromal cell-collagen mixture of step (b), thereby forming a middle stromal cell-collagen mixture layer provided on said inner layer;
   (d) culturing said inner endothelial cell layer and said middle layer;
   (e) contacting corneal epithelial cells onto said middle layer of step (d);
   (f) culturing said corneal epithelial cells with said middle layer until said middle layer is covered with an external layer of epithelial cells; and,
   (g) continue culturing said inner, middle, and external layers to form a cornea equivalent.

19. The method of claim 18, wherein said endothelial cells of step (a) are derived from a member selected from the group consisting of SCE2 which are ovine corneal endothelial cells, SCE 006A which are ovine arterial endothelial cells, SEC 023VC which are ovine endothelial cells, DVEC which are canine vena caval endothelial cells, HUVEC which are human umbilical vein endothelial cells and BCE 15960 which are bovine corneal endothelial cells.

20. The method as in either claim 18 or claim 19, wherein said endothelial cells of said endothelial cell layer are transformed with the large T antigen of SV40.

21. The method of claim 18, wherein said fibroblast cells of said middle stromal cell - collagen mixture layer are derived from the group comprising human dermal fibroblast cells, human corneal keratocytes, and rabbit corneal keratocytes.

22. The method of claim 18, wherein said epithelial cells of said external epithelial cell layer are derived from the group comprising corneal epithelial cells and scleral epithelial cells.

23. The method of claim 18, wherein said endothelial cells are cultured in said first step by contacting said endothelial cells onto a porous membrane attached to the bottom of a cell culture insert.

24. The method of claim 23, wherein said porous membrane has a porosity of from about 0.2 micrometers to 10 micrometers.

25. The method of claim 23, wherein prior to said contacting, an acellular collagen layer is cast onto said porous membrane.

26. The method of claim 18, wherein the collagen in said stromal cell collagen mixture is selected from the group consisting of acid extracted bovine tendon collagen, enzyme extracted bovine tendon collagen, rat tail collagen, Type I collagen extracted from dermis, Type III collagen extracted from dermis, Type I collagen extracted from corneal stroma, Type V collagen extracted from corneal stroma, Type VI collagen extracted from corneal stroma, and mixture thereof.

27. The method of claim 26, wherein said collagen is a mixture of Types I and III collagen extracted from dermis.

28. The method of claim 26, wherein said collagen is a mixture of Types I, V and VI collagen extracted from corneal stroma.

29. The method of claim 18, wherein said stromal cell-collagen mixture of said step (b) contains approximately 100 corneal stromal fibroblast cells per microgram collagen or $5 \times 10^4$ corneal stromal fibroblast cells/mL collagen and said collagen.

30. The method of claim 18, wherein said inner endothelial cell layer and said middle layer of said step (d) are cultured until said middle layer contracts to form a central raised area.

31. The method of claim 18, wherein said middle stromal cell-collagen mixture layer is uniform in thickness.

32. The method of claim 18, wherein said external epithelial cell layer is uniform in thickness.

33. The method of claim 18, wherein said epithelial cells in said step (e) are seeded on top of said middle layer of step (b) at a density of $7.2 \times 10^4 - 1.4 \times 10^5$ cells/ cm$^2$.

34. The method of claim 18, wherein a droplet of tear film is placed onto said external layer of epithelial cells or adding said tear film directly to the culture medium.

35. The method of claim 34, wherein said tear film comprises physiologic buffered salt solution.

36. The method of claim 35, wherein said physiologic buffered salt solution further comprises one or more components selected from the group consisting of protein-lipid surfactants, lipids, mucin, glycosaminoglycans, and hyaluronic acid.

* * * * *